United States Patent [19]

Nishimoto et al.

[11] Patent Number: 5,128,469
[45] Date of Patent: Jul. 7, 1992

[54] PROCESS FOR PREPARING 1,5-BENZOTHIAZEPINE DERIVATIVES

[75] Inventors: Shigeru Nishimoto, Minoo; Akio Nakao, Osaka; Yasuji Ikeda, Kyoto; Hiroyuki Nate, Higashiosaka; Hironori Hayashi, Toyonaka; Tamotsu Okuno, Kawanishi; Masashi Kitano, Nara; Sadao Maeda, Ibaraki, all of Japan

[73] Assignee: Tanabe Seiyaku Co., Ltd., Osaka, Japan

[21] Appl. No.: 722,497

[22] Filed: Jun. 26, 1991

Related U.S. Application Data

[63] Continuation-in-part of Ser. No. 516,938, Apr. 30, 1990, abandoned, and a continuation-in-part of Ser. No. 516,940, Apr. 30, 1990, Pat. No. 5,055,575, Ser. No. 516,938, Apr. 30, 1990, abandoned, which is a continuation-in-part of Ser. No. 507,929, Apr. 12, 1990, abandoned, Ser. No. 516,940, Apr. 30, 1990, Pat. No. 5,055,575, which is a continuation-in-part of Ser. No. 507,801, Apr. 12, 1990, abandoned.

[30] Foreign Application Priority Data

Apr. 28, 1989 [JP] Japan ................... 1-109794
Apr. 28, 1989 [JP] Japan ................... 1-109795

[51] Int. Cl.$^5$ .................... C07D 281/02; A61K 31/55
[52] U.S. Cl. .................................... 540/491
[58] Field of Search ........................ 540/491

[56] References Cited

U.S. PATENT DOCUMENTS

| | | | |
|---|---|---|---|
| 3,562,257 | 2/1971 | Kugita et al. | 540/491 |
| 4,438,035 | 3/1984 | Gaino et al. | 540/491 |
| 4,567,175 | 1/1986 | Takeda et al. | 514/211 |
| 4,590,188 | 5/1986 | Takeda et al. | 514/211 |
| 4,882,326 | 11/1989 | Murakami et al. | 514/211 |
| 5,013,835 | 5/1991 | Rossey et al. | 540/491 |

FOREIGN PATENT DOCUMENTS

| | | | |
|---|---|---|---|
| 0098422 | 1/1984 | European Pat. Off. | 540/491 |
| 0343474 | 11/1989 | European Pat. Off. | 540/491 |
| 0378455 | 7/1990 | European Pat. Off. | 540/491 |
| 46-43785 | 12/1971 | Japan | 540/491 |
| 53-18038 | 6/1978 | Japan | 540/491 |
| 2139620 | 11/1984 | United Kingdom | 540/491 |

*Primary Examiner*—Robert T. Bond
*Attorney, Agent, or Firm*—Browdy and Neimark

[57] ABSTRACT

This disclosure describes a process for the preparation of 1,5-benzothiazepinone derivatives. The process involves the use of sulfonic acids as catalysts to effect ring closure to form the 1,5-benzothiazepinone ring. The resulting compounds have well known pharmaceutical properties.

21 Claims, No Drawings

PROCESS FOR PREPARING 1,5-BENZOTHIAZEPINE DERIVATIVES

CROSS-REFERENCE TO RELATED APPLICATIONS

The present application is a continuation-in-part of application Ser. No. 07/516,938, filed Apr. 30, 1990, now abandoned, and application Ser. No. 07/516,940, filed Apr. 30, 1990, now U.S. Pat. No. 5,055,575, the entire contents of both of which are hereby incorporated by reference. Application Ser. No. 07/516,938 is a continuation-in-part of application Ser. No. 07/507,929, filed Apr. 12, 1990, now abandoned. Application Ser. No. 07/516,940 is a continuation-in-part of application Ser. No. 07/507,801, filed Apr. 12, 1990, now abandoned.

FIELD OF THE INVENTION

This invention relates to a novel process for preparing a 1,5-benzothiazepine derivative represented by the formula (I):

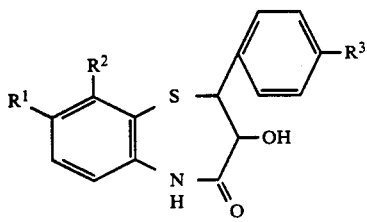

wherein
(A) one of $R^1$ and $R^2$ is a lower alkyl group or a halogen atom, and the other is a hydrogen atom; and $R^3$ is a lower alkyl group or a lower alkoxy group; or
(B) both of $R^1$ and $R^2$ are hydrogen atoms, and $R^3$ is a lower alkoxy group.

The above 1,5-benzothiazepine derivative (I) is useful as an intermediate for the synthesis of, for example, the corresponding 3-acetoxy-5-[2-(dimethylamino)ethyl]-1,5-benzothiazepine derivative having excellent coronary vasodilating or hypotensive activity.

BACKGROUND OF THE INVENTION

Heretofore, as a process for preparing a 1,5-benzothiazepine derivative (I), the method in which a propionic acid derivative represented by the formula (II):

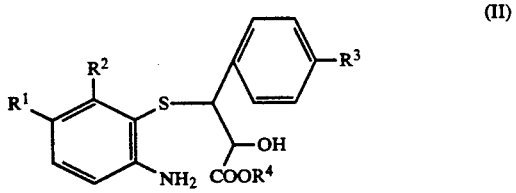

wherein
(A) one of $R^1$ and $R^2$ is a lower alkyl group or a halogen atom, and the other is a hydrogen atom; $R^3$ is a lower alkyl group or a lower alkoxy group; and $R^4$ is a hydrogen atom or an ester residue; or
(B) both of $R^1$ and $R^2$ are hydrogen atoms, $R^3$ is a lower alkoxy group, and $R^4$ is a hydrogen atom,
is heated in a solvent (e.g., xylene) to effect an intramolecular ring closing reaction has been known (U.S. Pat. No(s). 4,567,175 and 4,590,188, Japanese Patent Publication (examined) No. 18038/1978).

However, this method involves the problem of requiring a long period of time (e.g., 12 hours in Examples of the above-mentioned Japanese Patent Publication) for the intramolecular ring closing reaction.

SUMMARY OF THE INVENTION

As a result of their research, the present inventors have found that, when the intramolecular ring closing reaction of the compound (II) is carried out in the presence of a specific sulfonic acid compound, the compound (I) can be prepared within a short period of time in good yield. The present invention has been established based on such findings.

According to the process of the present invention, the 1,5-benzothiazepine derivative represented by the formula (I) can be prepared by subjecting a propionic acid derivative (II) or a salt thereof to intramolecular ring closing reaction in the presence of a sulfonic acid compound represented by the formula (III):

$$R^5SO_3H \qquad (III)$$

wherein $R^5$ is a lower alkyl group or a substituted or unsubstituted phenyl group.

DESCRIPTION OF THE PREFERRED EMBODIMENTS

Examples of the sulfonic acid compound (III) to be used in the intramolecular ring closing reaction of the present invention include the compounds in the formula (III) wherein $R^5$ is an alkyl group having one to 4 carbon atom(s) such as a methyl, ethyl, propyl or butyl group, or a phenyl group which may be substituted by at least one of these alkyl group(s). In particular, methanesulfonic acid or p-toluenesulfonic acid is preferably used. The amount of said sulfonic acid is not particularly limited but generally it is preferably used at an amount of 0.5 to 10 w/w%, more preferably about one to 6 w/w% based on the compound (II).

Examples of the ester residue which may be used in the compound (II) include conventional ester residues which may be removed in the process of amide formation. Among them, a substituted or unsubstituted lower alkyl group is preferably used. Examples of the salt of the compound (II) include conventional acid addition salts at the amino group thereof.

The present intramolecular ring closing reaction is preferably practiced in an appropriate solvent with heating, preferably under reflux. As the solvent, high boiling point organic solvents such as non-chlorinated organic solvents (e.g., xylene, toluene) and chlorinated organic solvents (e.g., dichlorobenzene) are preferably used. Among them, xylene is especially preferred. Reaction time may be extremely short as compared with the case where no sulfonic acid compound is used therein. For example, when xylene is used as a solvent, the reaction can be completed in about 30 minutes to about 4 hours.

The desired compound (I) can be isolated as a pure product containing no sulfonic acid compound (III) by simple and easy operations, for example, by cooling the reaction mixture, collecting precipitated crystals by filtration and washing them with a suitable solvent (e.g., ethanol, aqueous ethanol, etc.).

Moreover, since the process of the present invention can be conducted without racemization, the optical isomer of the 1,5-benzothiazepine derivative (I) is obtained by the use of the corresponding optical isomer of the propionic acid derivative (II) while a racemic mixture of the compound (I) is obtained by the use of the racemic mixture of the compound (II).

The thus obtained compound (I) can be converted to the corresponding 3-acetoxy-5-[2-(dimethylamino)ethyl]-1,5-benzothiazepine derivative represented by the formula (IV):

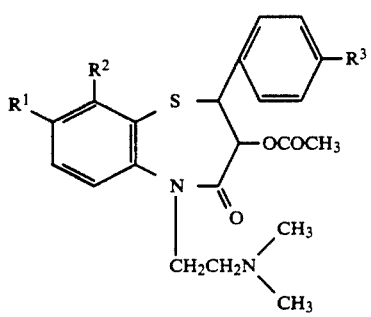

(IV)

wherein $R^1$, $R^2$ and $R^3$ are the same as defined above, or a pharmaceutically acceptable salt thereof according to known methods; for example, in a method described in U.S. Pat. No(s). 4,567,175, 4,590,188, 3,562,257 and 4,438,035 and Japanese Patent Publication (examined) Nos. 18038/1978 and 43785/1971, the contents of which are hereby incorporated by reference.

According to the process of the present invention, as mentioned above, the intramolecular ring closing reaction can be terminated within a short period of time and the desired compound can be obtained in high yield and high purity. Therefore, the process of the present invention is excellent from the industrial viewpoint as compared with the known process in which the reaction is carried out in the absence of the sulfonic acid compound.

The starting compound (II) can be prepared according to the method as disclosed in Japanese Patent Publication (examined) No. 18038/1978 and U.S. Pat. No(s). 4,567,175 and 4,590,188, but an optical isomer of the compound (II) wherein $R^4$ is an ester residue, i.e., an optically active threopropionic acid ester derivative represented by the formula (II-a):

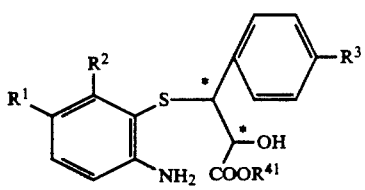

(II-a)

wherein $R^{4\,1}$ is an ester residue, asterisk represents that said carbon atom is an asymmetric carbon atom, and $R^1$, $R^2$ and $R^3$ are the same as defined above, can be prepared by reacting a thiophenol compound represented by the formula (V):

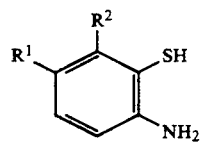

(V)

wherein $R^1$ and $R^2$ are the same as defined above, with an optically active trans-glycidic acid ester represented by the formula (VI):

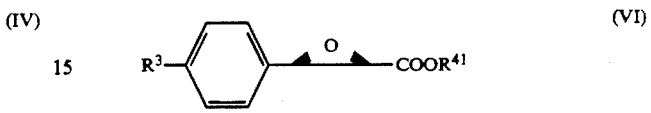

(VI)

wherein $R^3$ and $R^{4\,1}$ are the same as defined above.

Throughout the specification and claims, the terms "a lower alkyl group" and "a lower alkoxy group" should be interpreted as referring to an alkyl group of one to 4 carbon atom(s) and an alkoxy group of one to 4 carbon atom(s), respectively.

EXPERIMENTAL EXAMPLE

For forming (+)-cis-2-(4-methoxyphenyl)-3-hydroxy-2,3-dihydro-1,5-benzothiazepin-4(5H)-one by refluxing by heating 12.75 g of (+)-threo-2-hydroxy-3-(2-aminophenylthio)-3-(4-methoxyphenyl)propionic acid in 52 ml of xylene or toluene, under continuous removal of formed water, the effects of presence of a sulfonic acid compound in the reaction system were examined. The results are shown in Tables 1 and 2.

In the tables, the amount of the sulfonic acid compound is based on the starting compound, and p-toluenesulfonic acid is used as a monohydrate.

TABLE 1

| | (in xylene) | | | |
|---|---|---|---|---|
| | Sulfonic acid compound | Amount used (w/w %) | Reaction time | Yield of desired product (%) |
| Process of this invention | p-Toluenesulfonic acid | 5.4 | 30 min | 94 |
| | | 2.7 | 60 min | 93.9 |
| | | 1.1 | 1 hr & 15 min | 95.5 |
| | | 0.6 | 2 hrs & 15 min | 95.4 |
| | Methanesulfonic acid | 5.4 | 45 min | 93 |
| Control* | — | — | 12 hrs | 82.2 |

*Control is Example described in Japanese Patent Publication (examined) No. 18038/1978

TABLE 2

| | (in toluene) | | | |
|---|---|---|---|---|
| | Sulfonic acid compound | Amount used (w/w %) | Reaction time | Yield of desired product (%) |
| Process of this invention | p-Toluenesulfonic acid | 5.4 | 5 hrs | 92 |
| | Methanesulfonic acid | 5.4 | 5 hrs | 92 |
| Control | — | — | 7 hrs | <50 |

As seen from the above Table 1 and Table 2, it can be understood that by the existence of p-toluenesulfonic acid or methanesulfonic acid in the reaction system, the desired product can be obtained within an extremely short time in good yield.

EXAMPLE 1

A mixture of 12.75 g of (+)-threo-2-hydroxy-3-(2-amino-phenylthio)-3-(4-methoxyphenyl)propionic acid, 140 mg of p-toluenesulfonic acid monohydrate and 52 ml of xylene is refluxed by heating for about 1 hour and 15 minutes. During the reaction, water formed is continuously removed. After cooling, precipitated crystals are collected by filtration and washed with cooled ethanol to give 11.5 g of (+)-cis-2-(4-methoxyphenyl)-3-hydroxy-2,3-dihydro-1,5-benzothiazepin-4(5H)-one.

Yield: 95.5%
m.p.: 203 to 204° C.
$[\alpha]_D^{20} + 116°$ (c=0.5, dimethylformamide)

EXAMPLE 2

A mixture of 12.75 g of (+)-threo-2-hydroxy-3-(2-amino-phenylthio)-3-(4-methoxyphenyl)propionic acid, 690 mg of p-toluenesulfonic acid monohydrate and 52 ml of toluene is refluxed by heating for about 5 hours. During the reaction, water formed is continuously removed. After cooling, precipitated crystals are collected by filtration and washed with cooled ethanol to give 11 g of (+)-cis-2-(4-methoxyphenyl)-3-hydroxy-2,3-dihydro-1,5-benzothiazepin-4(5H)-one.

Yield: 92%
m.p.: 203 to 204.5° C.
$[\alpha]_D^{20} + 118°$ (c=0.5, dimethylformamide)

EXAMPLE 3

(1) In 400 ml of toluene are dissolved 24.0 g of 2-amino-5-chlorothiophenol and 31.2 g of (−)-trans-3-(4-methoxyphenyl)glycidic acid methyl ester and the solution is refluxed under nitrogen atmosphere for 2 hours. Diisopropyl ether is added to the reaction mixture, and precipitated crystals are collected by filtration to give 37.6 g of (+)-threo-2-hydroxy-3-(2-amino-5-chlorophenylthio)-3-(4-methoxyphenyl)propionic acid methyl ester as colorless needles.

Yield: 68%
m.p.: 126 to 129.5° C.
$[\alpha]_D^{20} + 248.8°$ (c=0.3, methanol)

(2) A mixture of 9.5 g of the present product, 0.49 g of p-toluenesulfonic acid monohydrate and 95 ml of xylene is refluxed for 2 hours. After cooling, precipitated crystals are collected by filtration to give 7.5 g of (+)-cis-2-(4-methoxyphenyl)-3-hydroxy-8-chloro-2,3-dihydro-1,5-benzothiazepin-4(5H)-one.

Yield: 86.8%
m.p.: 244 to 245° C.
$[\alpha]_D^{20} + 91.6°$ (c=1.0, dimethylformamide)

EXAMPLE 4

A mixture of 17.0 g of (+)-threo-2-hydroxy-3-(2-amino-5-chlorophenylthio)-3-(4-methoxyphenyl)propionic acid, 0.91 g of p-toluenesulfonic acid monohydrate and 220 ml of xylene is refluxed for 2 hours under continuous removal of water. After cooling, precipitated crystals are collected by filtration and washed with ethanol to give 15 g of (+)-cis-2-(4-methoxyphenyl)-3-hydroxy-8-chloro--2,3-dihydro-1,5-benzothiazepin-4(5H)-one.

Yield: 93%
m.p. 244 to 245° C.

Incidentally, according to the method in which the above reaction is practiced in the absence of p-toluenesulfonic acid in the same manner as described in Japanese Provisional Patent Publication No. 225174/1984, the yield of the desired compound is only 73% even after refluxing for 20 hours.

EXAMPLE 5

A mixture of 17.0 g of (+)-threo-2-hydroxy-3-(2-amino-5-chlorophenylthio)-3-(4-methoxyphenyl)propionic acid, 0.91 g of p-toluenesulfonic acid monohydrate and 220 ml of toluene is refluxed for 8 hours under continuous removal of water. After cooling, precipitated crystals are collected by filtration and washed with ethanol to give 14.8 g of (+)-cis-2-(4-methoxyphenyl)-3-hydroxy-8-chloro-2,3-dihydro-1,5-benzothiazepin-4(5H)-one.

Yield: 92%
m.p. 244 to 245° C.

EXAMPLE 6

(1) In 600 ml of xylene are dissolved 132 g of 2-amino-5-methylthiophenol and 200 g of (±)-trans-3-(4-methylphenyl)glycidic acid methyl ester and the solution is refluxed at 120 to 130° C. under nitrogen atmosphere for 4 hours. After cooling to 40° C., n-hexane is added to the reaction mixture, and the reaction mixture is stirred and then cooled to 10° C.. Precipitated crystals are collected by filtration to give 218 g of (±)-threo-2-hydroxy-3-(2-amino-5-methylphenylthio)-3-(4-methylphenyl)propionic acid methyl ester as colorless crystals.

Yield: 69%
m.p. 114 to 116° C.

(2) In 500 g of xylene are dissolved 50 g of the product; 0.57 g of p-toluenesulfonic acid monohydrate is added to the solution and the solution is refluxed for 4 hours. After cooling, precipitated crystals are collected by filtration, washed with xylene to give 39.0 g of (±)-cis-2-(4-methylphenyl)-3-hydroxy-8-methyl-2,3-dihydro-1,5-benzothiazepin-4(5H)-one as colorless crystals.

Yield: 86%
m.p 185 to 186° C.

EXAMPLE 7

In a solution of 200 ml of water and 100 g of methanol are suspended 40 g of (±)-threo-2-hydroxy-3-(2-amino-5-methyl-phenylthio)-3-(4-methylphenyl)propionic acid methyl ester; 7.4 g of potassium hydroxide are added to the suspension and the mixture is stirred for 30 minutes at 50 to 55° C. Then, 13.8 g of 35% hydrochloric acid are added dropwise, and 200 ml of water are added thereto, and the mixture is cooled to 10° C. Precipitated crystals are collected by filtration and washed with water to give 80 g of (±)-threo-2-hydroxy-3-(2-amino-5-methylphenylthio)-3-(4-methylphenyl)propionic acid (wet material).

This product (80 g) is suspended in 400 ml of toluene, and 0.4 g of p-toluenesulfonic acid monohydrate is added thereto and the mixture is refluxed for 5 hours under continuous removal of water. After cooling, precipitated crystals are collected by filtration, washed with toluene and dried to give 32.5 g of (±)-cis-2-(4-methylphenyl)-3-hydroxy-8-methyl-2,3-dihydro-1,5-benzothiazepin-4(5H)-one.

Yield: 90%
m.p. 185 to 186° C.

EXAMPLE 8

In 400 ml of toluene are dissolved 24.0 g of 2-amino-5-chlorothiophenol and 31.2 g of (4-methoxyphenyl)glycidic acid methyl ester, and the solution is refluxed under nitrogen atmosphere for 2 hours. To the reaction mixture are added 1.43 g of p-toluenesulfonic acid hydrate and 350 ml of xylene and the mixture is refluxed for 2 hours and simultaneously 350 ml of the solvent is distilled. After cooling, precipitated crystals are collected by filtration to give 19.8 g of (+)-cis-2-(4-methoxyphenyl)-3-hydroxy-8-chloro-2,3-dihydro-1,5-benzothiazepin-4(5H)-one.

Physical and chemical properties of the product were identical to those of the product obtained in Example 3.

EXAMPLE 9

(1) In 420 ml of xylene are dissolved 42 g of 2-amino-5-methylthiophenol and 58 g of (+)-trans-3-(4-methylphenyl)-glycidic acid methyl ester, and the solution is refluxed under nitrogen atmosphere for 2 hours. After cooling, n-hexane is added to the reaction mixture and precipitated crystals are collected by filtration to give 65 g of (±)-threo-2-hydroxy-3-(2-amino-5-methylphenylthio)-3-(4-methylphenyl)-propionic acid methyl ester as colorless needles.

Yield: 65%
m.p. 107 to 109° C.
$[\gamma]_D^{20} - 235.4°$ (c=1, methanol)

(2) A mixture of 20 g of the above product, 0.4 g of p-toluenesulfonic acid monohydrate and 160 ml of xylene is refluxed for 5 hours. After cooling, precipitated crystals are collected by filtration to give 15.7 g of (−)-cis-2-(4-methylphenyl)-3-hydroxy-8-methyl-2,3-dihydro-1,5-benzothiazepin-4(5H)-one.

Yield: 87%
m.p. 207 to 212° C.
$[\gamma]_D^{20} - 120°$ (c =0.3, methanol)

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

We claim:

1. A process for preparing a 1,5-benzothiazepine represented by the formula (I):

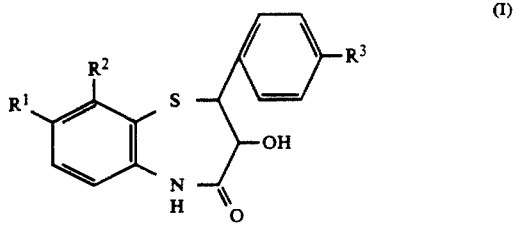

wherein
(A) one of $R^1$ and $R^2$ is a lower alkyl group or a halogen atom, and the other is a hydrogen atom; and $R^3$ is a lower alkyl group or a lower alkoxy group; or (B) both of $R^1$ and $R^2$ are hydrogen atoms; and $R^3$ is a lower alkoxy group, which consists essentially of subjecting a propionic acid compound represented by the formula (II):

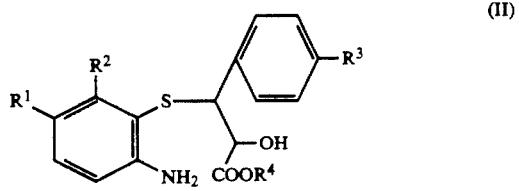

wherein
(A) one of $R^1$ and $R^2$ is a lower alkyl group or a halogen atom, and the other is a hydrogen atom; $R^3$ is a lower alkyl group or a lower alkoxy group; and $R^4$ is a hydrogen atom or an ester residue; or
(B) both of $R^1$ and $R^2$ are hydrogen atoms; $R^3$ is a lower alkoxy group; and $R^4$ is a hydrogen atom,
or a salt thereof, to an intramolecular ring closing reaction in the presence of a sulfonic acid compound represented by the formula (III):

$R^5SO_3H$ (III)

wherein $R^5$ is a lower alkyl group or a substituted or unsubstituted phenyl group.

2. The process according to claim 1, wherein one of $R^1$ and $R^2$ is a lower alkyl group or a halogen atom, and the other is a hydrogen atom; $R^3$ is a lower alkyl group or a lower alkoxy group; and $R^4$ is a hydrogen atom or an ester residue.

3. The process according to claim 1, wherein all of $R^1$, $R^2$ and $R^4$ are hydrogen atoms, and $R^3$ is a lower alkoxy group.

4. The process according to claim 1, wherein $R^5$ in the sulfonic acid compound (III) is a methyl, ethyl, propyl or butyl group or a phenyl group which may be substituted by at least one moiety selected from the group consisting of methyl, ethyl, propyl and butyl moieties.

5. The process according to claim 2, wherein $R^5$ in the sulfonic acid compound (III) is a methyl, ethyl, propyl or butyl group or a phenyl group which may be substituted by at least one moiety selected from the group consisting of methyl, ethyl, propyl and butyl moieties.

6. The process according to claim 3, wherein $R^5$ in the sulfonic acid compound (III) is a methyl, ethyl, propyl or butyl group or a phenyl group which may be substituted by at least one moiety selected from the group consisting of methyl, ethyl, propyl and butyl moieties.

7. The process according to claim 4, wherein the sulfonic acid compound (III) is methanesulfonic acid or p-toluenesulfonic acid.

8. The process according to claim 5, wherein the sulfonic acid compound (III) is methanesulfonic acid or p-toluenesulfonic acid.

9. The process according to claim 6, wherein the sulfonic acid compound (III) is methanesulfonic acid or p-toluenesulfonic acid.

10. The process according to claim 1, wherein the reaction is carried out in an appropriate solvent with heating.

11. The process according to claim 2, wherein the reaction is carried out in an appropriate solvent with heating.

12. The process according to claim 3, wherein the reaction is carried out in an appropriate solvent with heating.

13. The process according to claim 1, wherein the sulfonic acid compound (III) is used in an amount of 0.5 to 10 w/w% based on the compound (II).

14. The process according to claim 2, wherein the sulfonic acid compound (III) is used in an amount of 0.5 to 10 w/w% based on the compound (II).

15. The process according to claim 3, wherein the sulfonic acid compound (III) is used in an amount of 0.5 to 10 w/w% based on the compound (II).

16. The process according to claim 13, wherein the sulfonic acid compound (III) is used in an amount of one to 6 w/w% based on the compound (II).

17. The process according to claim 14, wherein the sulfonic acid compound (III) is used in an amount of one to 6 w/w% based on the compound (II).

18. The process according to claim 15, wherein the sulfonic acid compound (III) is used in an amount of one to 6 w/w% based on the compound (II).

19. A process for preparing a 3-acetoxy-5-[2-(dimethylamino)ethyl]-1,5-benzothiazepine represented by the formula (IV):

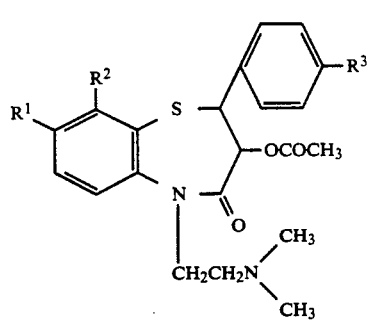

wherein
(A) one of $R^1$ and $R^2$ is a lower alkyl group or a halogen atom, and the other is a hydrogen atom; and $R^3$ is a lower alkyl group or a lower alkoxy group; or
(B) both of $R^1$ and $R^2$ are hydrogen atoms, and $R^3$ is a lower alkoxy group,
or a pharmaceutically acceptable salt thereof which consists essentially of subjecting a propionic acid compound represented by the formula (II):

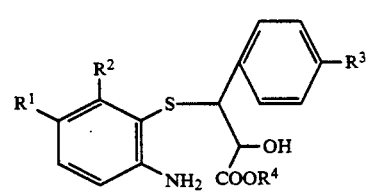

wherein
(A) one of $R^1$ and $R^2$ is a lower alkyl group or a halogen atom, and the other is a hydrogen atom; $R^3$ is a lower alkyl group or a lower alkoxy group; and $R^4$ is a hydrogen atom or an ester residue; or
(B) both of $R^1$ and $R^2$ are hydrogen atoms; $R^3$ is a lower alkoxy group; and $R^4$ is a hydrogen atom,
or a salt thereof to intramolecular ring closing reaction in the presence of a sulfonic acid compound represented by the formula (III):

$R^5SO_3H$ (III)

wherein $R^5$ is a lower alkyl group or a substituted or unsubstituted phenyl group, to give a compound represented by the formula (I):

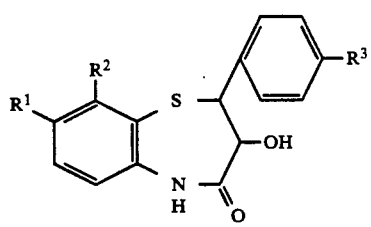

wherein $R^1$, $R^2$ and $R^3$ are the same as defined above, and subjecting the compound (I) to 2-(dimethylamino)ethylation and acetylation, and, optionally, further converting the product to a pharmaceutically acceptable salt thereof.

20. The process according to claim 19, wherein one of $R^1$ and $R^2$ is a lower alkyl group or a halogen atom, and the other is a hydrogen atom; $R^3$ is a lower alkyl group or a lower alkoxy group; and $R^4$ is a hydrogen atom or an ester residue.

21. The process according to claim 19, wherein all of $R^1$, $R^2$ and $R^4$ are hydrogen atoms, and $R^3$ is a lower alkoxy group.

* * * * *